United States Patent [19]
Nonaka et al.

[11] 3,943,161
[45] Mar. 9, 1976

[54] PROCESS FOR PRODUCING CONJUGATED DIENES CONTAINING A CYANO GROUP

[75] Inventors: Yuji Nonaka; Keiichi Kihara; Toshio Hironaka; Yasuhiro Oda, all of Shin-nanyo, Japan

[73] Assignee: Toyo Soda Manufacturing Co., Ltd., Japan

[22] Filed: Nov. 27, 1974

[21] Appl. No.: 527,653

[30] Foreign Application Priority Data
Nov. 27, 1973 Japan.............................. 48-132195

[52] U.S. Cl............................ 260/465 K; 260/465.9
[51] Int. Cl.². ............C07C 120/00; C07C 121/30; C07C 121/52
[58] Field of Search...................... 260/465.9, 465 K

[56] References Cited
UNITED STATES PATENTS

| | | | |
|---|---|---|---|
| 2,375,005 | 5/1945 | Kung............................ | 260/465.9 X |
| 2,500,403 | 3/1950 | Davis et al...................... | 260/465.9 |
| 2,503,710 | 4/1950 | Bruson............................ | 260/465.9 |

*Primary Examiner*—Joseph P. Brust
*Attorney, Agent, or Firm*—Oblon, Fisher, Spivak, McClelland & Maier

[57] ABSTRACT

Conjugated dienes containing a cyano group having the formula

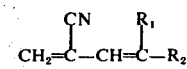

wherein $R_1$ and $R_2$ represent hydrogen atom, an alkyl group or a phenyl group are produced by dehydrating 2-cyano-3-hydroxy-1-olefins in the presence of an alkaline catalyst while continually removing the product being formed from the reaction system.

7 Claims, No Drawings

PROCESS FOR PRODUCING CONJUGATED DIENES CONTAINING A CYANO GROUP

BACKGROUND OF THE INVENTION

1. Field of the Invention

The present invention relates to a novel process for producing a conjugated diene containing a cyano group having the formula

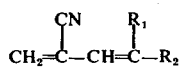

wherein $R_1$ and $R_2$ represent a hydrogen atom, an alkyl group or a phenyl group.

2. Description of the Prior Art

These compounds produced by the process of this invention are useful as monomers or comonomers for preparing plastics or elastomers. The conjugated diene having a cyano group wherein $R_1$ and $R_2$ are hydrogen atoms, i.e., 2-cyano-1,3-butadiene, is especially useful. Various schemes for syntheses have been proposed. Typical of these are:

1. Preparing methyl vinyl ketone cyanohydrin by reacting methyl vinyl ketone with hydrogen cyanide, and thereafter acetylating to produce 3-acetoxy-3-cyano-butene-1. 2-Cyano-1,3-butadiene is then produced by the thermal decomposition of the product at 550°–570°C [disclosed in B.P. 482,300, *J. Am. Chem. Soc.* 70, 1775 (1948) and U.S. Pat. No. 2,205,239].

2. Methyl vinyl ketone cyanohydrin is selectively dehydrated at 400°–700°C in the presence of phosphoric acid. [disclosed in West German Pat. No. 1,081,006 and West German Pat. No. 1,113,216.]

3. Preparing 2-cyano-1,3-butadiene by dehydrocyanation of 1,2-dicyano-cyclobutane in the presence of a solid alkaline oxide catalyst. [disclosed in U.S. Pat. No. 3,347,902.]

However, the present invention for producing 2-cyano-1,3-butadiene and similar compounds is quite different from the abovementioned conventional processes.

The 2-cyano-3-hydroxy-1-olefin compounds used as the starting material of this invention are alcohols. In a synthesis of an olefin by the dehydration of an alcohol, it is customary to use as a catalyst a Bronsted acid, e.g., sulfuric acid, phosphoric acid, or a Lewis acid, e.g., zinc chloride, iodine, together with either an acid anhydride, e.g., boric anhydride, phthalic anhydride, acetic anhydride or phosphorus pentoxide, phosphorous trichloride, etc. as a dehydrating agent. It is also well-known to use alumina, silica gel or thorium oxide as carriers for solid catalysts. Consequently, it might be expected that a conjugated diene containing a cyano group could be produced by the dehydration of the starting compound in the presence of such an acidic catalyst. To the contrary, it has been found unexpectedly that such a dehydration is inhibited in the presence of an acid. Experimental acid dehydrations of 2-cyano-3-hydroxy-1-olefin compounds either could not be effected or produced only quite small yields. When a solid acidic catalyst is used, it has been found that a small amount of the cyano-containing conjugated diene is produced at the initiation of the reaction. However, this could not be put to industrial use because only thermal decomposition of the compound is involved.

It has been attempted to produce conjugated dienes containing a cyano group from 2-cyano-3-hydroxy-1-olefins using other schemes. As a result, it was found that 1,8-diaza-bicyclo[5,4,0] undecene-7 has catalytic action for the dehydration of 2-cyano-3-hydroxy-1-olefin compounds. As a result of further studies, the unexpected fact that catalytic dehydration of 2-cyano-3-hydroxy-1-olefin compound can be effected by using an alkaline material was discovered. To our knowledge, no other similar reaction, i.e., dehydration of secondary alcohol by alkaline catalyst, has been reported. Evidently, catalytic dehydration of 2-cyano-3-hydroxy-1-olefin compounds is a very unique dehydration, because the closely related compounds having the formula

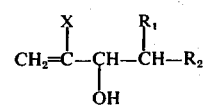

wherein X represents

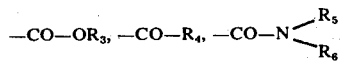

and $R_3$–$R_6$ represent alkyl groups, could not be converted to the corresponding conjugated dienes by using an alkaline catalyst. It would be most desirable to take advantage of this novel finding to provide an alternate scheme for producing the cyano-containing conjugated dienes.

SUMMARY OF THE INVENTION

Accordingly, it is an object of this invention to provide a very economical process for producing a conjugated diene containing a cyano group.

This and other objects of the invention, as will hereinafter be made clear by the discussion below, have been attained by providing a process for producing a conjugated diene containing a cyano group having the formula:

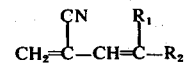

wherein $R_1$ and $R_2$ represent hydrogen atom, an alkyl group, preferably a lower $C_1$-$C_{10}$ alkyl group, or a phenyl group, by dehydrating a 2-cyano-3-hydroxy-1-olefin compound having the formula

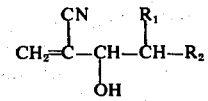

in the presence of an alkaline material while continuously removing the product from the reaction system.

DETAILED DESCRIPTION OF THE PREFERRED EMBODIMENTS

In the process of this invention, 2-cyano-3-hydroxy-1-olefin compound is heated under reduced pressure in the presence of an alkaline material while continuously removing the resulting conjugated diene containing a cyano group from the reaction system. The reaction can be performed in a liquid phase.

The structure of the conjugated dienes containing a cyano group can be confirmed by elementary analysis, infrared spectroscopic analysis and magnetic resonance spectroscopic analysis.

The 2-cyano-3-hydroxy-1-olefins having the formula

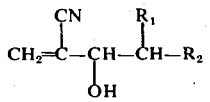

wherein $R_1$ and $R_2$ are defined above, can be easily produced by reacting acrylonitrile with an aldehyde having the formula

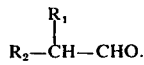

Suitable 2-cyano-3-hydroxy-1-olefins are 2-cyano-3-hydroxy-1-butene, 2-cyano-3-hydroxy-1-pentene, 2-cyano-3-hydroxy-4-methyl-1-pentene, 2-cyano-3-hydroxy-4-phenyl-1-butene, etc. All can be converted to the corresponding conjugated dienes containing a cyano group such as 2-cyano-1,3-butadiene, 2-cyano-1,3-pentadiene, 2-cyano-4-methyl-1,3-pentadiene, 2-cyano-4-phenyl-1,3-butadiene, etc. Suitable alkaline materials for use in the invention are those having catalytic activity such as alkali metals, alkaline earth metals, their hydroxides, oxides, inorganic salts, organic salts and alkoxides or organic amines, organic phosphines, etc. It is preferable to use alkaline materials which will not be easily removed from the reaction system under the conditions employed by becoming entrained in the resulting conjugated diene containing a cyano group. However, some alkaline materials which are easily separated from the resulting conjugated diene containing a cyano group are volatile under the reaction conditions. Consequently, it is especially preferable to use alkali metal salts such as sodium carbonate, sodium hydrogen carbonate, potassium carbonate, potassium hydrogen carbonate, sodium potassium carbonate, sodium silicate, potassium silicate, sodium borate, potassium borate, sodium phosphate, potassium phosphate, etc. An aqueous solution of the alkali metal salt is especially preferable for producing 2-cyano-1,3-butadiene from 2-cyano-3-hydroxy-1-butene. The alkaline materials can alternately be supported on a carrier. The catalysts can be prepared in several ways: by dissolving the alkaline material in water or in an organic solvent and dipping a carrier into the solution followed by concentration and drying; by pouring a solution of the alkaline material or the alkaline material itself onto a carrier and drying; or by mixing the alkaline material with silica sol or the like followed by concentrating, drying, calcining and crushing. The carriers can be made of alumina gel, silica gel, alumina-silica gel, activated carbon, diatomaceous earth, silicate, pumice, zeolite, etc. The catalyst can be in the form of powder, granules, blocks, etc.

The amount of the alkaline materials used relative to the 2-cyano-3-hydroxy-1-olefin compound is usually 0.1 – 20 wt %, preferably 0.3 – 6 wt %. The dehydration is performed at 50°–200°C, preferably under a reduced pressure of 1–600 mm Hg, preferably 20–200 mm Hg. When the alkaline material is used directly, the reaction temperature is preferably 80°–110°C. When the alkaline material is used as an aqueous solution, the reaction temperature is preferably 80°–120°C. When the alkaline material is supported on a carrier, the reaction temperature is preferably 80°–150°C.

In carrying out the invention, the alkaline material is added to the 2-cyano-3-hydroxy-1-olefin compound and the mixture is heated under reduced pressure to distill the resulting conjugated diene containing a cyano group. When a non-volatile alkaline material is used as the catalyst in the reaction, the reduced pressure can be selected so as to easily distill the product. When a volatile alkaline material is used, the reduced pressure is preferably selected low enough so as to easily distill the product, but not low enough to distill the alkaline material. The optimum reaction temperature is determined by the type of 2-cyano-3-hydroxy-1-olefin compound and the type and amount of catalyst. For example, the dehydration of 2-cyano-3-hydroxy-1-butene is performed at 50°–200°C, and especially at 80°–110°C in the case wherein 1,8-diaza-bicyclo [5,4,0] undecene-7 or potassium carbonate is used as the catalyst. In the gaseous phase method of the invention, the 2-cyano-3-hydroxy-1-olefin is fed onto a solid alkaline catalyst where it is converted to a conjugated diene containing a cyano group. The reaction temperature is selected depending upon the type of starting material and catalyst and is preferably 200°–600°C.

The following characteristics of the invention are especially noteworthy:

1. The reaction can be effectively performed in a batch system as well as in a semi-continuous system or a continuous system
2. A medium is not always required, however, an inert medium can be used
3. The yield of the conjugated diene may be increased by adding a polymerization inhibitor.

The process of the present invention will be illustrated by reference to certain specific examples, which are included for purposes of illustration only and are not intended to be limiting unless otherwise specified.

EXAMPLE 1

In a 200 cc round bottom flask equipped with a magnetic stirrer and a Liebig condenser, 150 g of 2-cyano-3-hydroxy-1-butene and 10 g of 1,8-diaza-bicyclo [5,4,0] undecene-7 were charged and the mixture was heated at 104°–110°C under the reduced pressure of 30–40 mm Hg produced by a water jet pump for about 1.5 hours to produce 75 g of distillate. The distillate was separated into a water phase and an organic phase. From the organic phase, 53 g of 2-cyano-1,3-butadiene was obtained. In all of the following Examples, the reactor of Example 1 was employed.

EXAMPLE 2

3 G of anhydrous potassium carbonate was added to 150 g of 2-cyano-3-hydroxy-1-butene, and the mixture was heated at 105°–110°C under the reduced pressure of 30 mm Hg produced by the water jet pump, while stirring for about 1 hour to give 84 g of a distillate. From the distillate 61 g of 2-cyano-1,3-butadiene was obtained.

EXAMPLE 3

A solution of 0.7 g of sodium hydroxide in 0.6 g of water was added to 150 g of 2-cyano-3-hydroxy-1-butene to form a homogeneous mixture and the mixture was heated at 80°C under the reduced pressure of 30 mm Hg produced by the water jet pump, while stirring for about 3 hours to give 31 g of 2-cyano-1,3-butadiene.

EXAMPLE 4

2 G of tri-n-butyl phosphine was added to 150 g of 2-cyano-3-hydroxy-1-butene and the mixture was heated at 80°C under the reduced pressure of 30–40 mm Hg produced by the water jet pump, while stirring for about 5.5 hours to give 13 g of 2-cyano-1,3-butadiene.

EXAMPLE 5

1 G of anhydrous potassium carbonate was added to 31 g of 2-cyano-3-hydroxy-1-pentene and the mixture was heated at 120°C under the reduced pressure of 30–35 mm Hg produced by the water jet pump for 45 minutes to give 19 g of 2-cyano-1,3-pentadiene.

EXAMPLE 6

2 G of anhydrous potassium carbonate was added to 31 g of 2-cyano-3-hydroxy-4-methyl-1-pentene and the mixture was heated at 120°–140°C under the reduced pressure of 45–60 mm Hg produced by the water jet pump for 2 hours to give 9 g of 2-cyano-4-methyl-1,3-pentadiene.

EXAMPLE 7

2 G of potassium hydroxide was added to 13 g of 2-cyano-3-hydroxy-4-phenyl-1-butene and the mixture was heated from 110°–160°C under the reduced pressure of 4 mm Hg to give 1.2 g of distillate. According to a gas-chromatographic analysis and a mass spectrographic analysis, the production of 0.18 g of 2-cyano-4-phenyl-1,3-butadiene was confirmed.

EXAMPLE 8

Silica gel was crushed into particles having 8–10 mesh size, and was immersed in a 20% aqueous solution of sodium hydroxide and then was dried at 130°C for 12 hours and calcined at 800°C for 3 hours to produce the catalyst. 60 ml of the catalyst was placed in a quartz reaction tube and was heated at 300°C. 2-Cyano-3-hydroxy-1-butene was flowed at a rate of 3.5 g per hour and nitrogen gas was flowed at a rate of 150 ml per minute for 2 hours. The gas discharged from the reaction tube was cooled by a methanol-dry ice trap to give 5.4 g of a condensed liquid. According to a gas-chromatographic analysis by the inner standard method, the producition of 0.28 g of 2-cyano-1,3-butadiene was confirmed.

EXAMPLES 9–22

In accordance with the process of Example 1, under modified conditions, 150 g of 2-cyano-3-hydroxy-1-butene was dehydrated. The conditions and the results are shown in Table 1.

Table 1

| Example | Catalyst | Amount of catalyst (g) | Temperature (°C) | Reduced pressure (mmHg) | Period for reaction (hrs) | Yield (g) |
| --- | --- | --- | --- | --- | --- | --- |
| 9 | KOH | 0.9 | 80 | 30 | 3.5 | 33 |
| 10 | tri-n-butylamine | 29 | 105–110 | 30–40 | 5.5 | 11 |
| 11 | NaHCO$_3$ | 3 | 105–110 | 30 | 5.5 | 52 |
| 12 | triethylenediamine | 8 | 105–110 | 20–40 | 5.5 | 40 |
| 13 | triethanolamine | 8.7 | 105–110 | 30–40 | 5.5 | 4 |
| 14 | Ba(OH)$_2$ | 5 | 85–90 | 30–40 | 4 | 46 |
| 15 | Ca(OH)$_2$ | 20 | 150 | 120–140 | 3.5 | 68 |
| 16 | Mg(OH)$_2$ | 20 | 120–170 | 30–150 | 5.5 | 6 |
| 17 | diethyl cyclohexylamine | 9 | 105–110 | 30–40 | 5.5 | 5 |
| 18 | dimethyl benzylamine | 19 | 105–110 | 30–40 | 5.5 | 2 |
| 19 | n-octylamine | 19 | 105–110 | 30–40 | 5.5 | 5 |
| 20 | 50% Na methoxide-methanol solution | 4.8 | 80 | 30 | 1.75 | 33 |
| 21 | sodium metal | 0.85 | 80–90 | 30 | 1 | 33 |
| 22 | potassium acetate | 13 | 90–140 | 30–80 | 4 | 58 |

REFERENCE 1

0.2 Cc of conc. sulfuric acid was added dropwise to 10 g of 2-cyano-3-hydroxy-1-butene while stirring and then the mixture was heated at 120°C. No production of 2-cyano-1,3-butadiene could be detected.

REFERENCE 2

136 G of conc. sulfuric acid was added to 74 g of water and the resultant solution was added to an ice-cooled 77 g of 2-cyano-3-hydroxy-1-butene while stirring. The solution was heated at 105°–110°C under the pressure of 30–40 mm Hg produced by the water jet pump for 5.5 hours. As a result, only 0.4 g of 2-cyano-1,3-butadiene was produced and no starting material was recovered.

REFERENCE 3

0.5 G of iodine was added to 100 g of 2-cyano-3-hydroxy-1-butene and the mixture was heated at 105°–110°C under the reduced pressure of 30–40 mm Hg produced by the water jet pump. As a result, no 2-cyano-1,3-butadiene was produced and all of the starting material was recovered.

EXAMPLE 23

In a 100 cc round bottom flask equipped with a magnetic stirrer and a Liebig condenser, 50 g of 2-cyano-3-hydroxy-1-butene and a solution of 1 g of potassium carbonate in 5 g of water were charged and the mixture was heated at 105°C under the reduced pressure of 30 mm Hg produced by a water jet pump for about 48 minutes to give 40.3 g of a distillate. The distillate was separated into a water phase and an organic phase. From the organic phase, 27.7 g of 2-cyano-1,3-butadiene was obtained (Yield 68%). In said process, 1 g of anhydrous potassium carbonate was added, whereby 30.9 g of distillate was produced in about 48 minutes. 24.0 g of 2-cyano-1,3-butadiene was obtained from the distillate (Yield 59%).

EXAMPLE 24

The process of Example 23 was repeated except for the addition of a solution of 1 g of potassium carbonate in 10 g of water, whereby 45.8 g of distillate was produced in about 46 minutes. 27.4 g of 2-cyano-1,3-butadiene was obtained from the distillate (Yield 67%).

EXAMPLE 25

The process of Example 23 was repeated except for the addition of a solution of 1 g of potassium carbonate in 1 g of water, whereby 38.0 g of distillate was produced in about 30 minutes. 28.0 g of 2-cyano-1,3-butadiene was obtained from the distillate (Yield 69%).

EXAMPLE 26

The process of Example 23 was repeated except for the addition of a solution of 1 g of potassium carbonate in 2 g of water, whereby 39.9 g of distillate was produced in about 34 minutes. 29.3 g of 2-cyano-1,3-butadiene was obtained from the distillate (Yield 72%).

EXAMPLE 27

The process of Example 23 was repeated except for the addition of a solution of 0.2 g of potassium carbonate in 1 g of water, and the heating to a temperature of 138°–140°C under the reduced pressure of 70 mm Hg produced by the water jet pump, whereby 38.7 g of a distillate was produced in about 30 minutes. 28.5 g of 2-cyano-1,3-butadiene was obtained from the distillate (Yield 70%).

EXAMPLE 28

The process of Example 23 was repeated except for the addition of a solution of 1 g of sodium hydrogen carbonate in 15 g of water while stirring at room temperature and heating at 105°–110°C under the pressure of 30 mm Hg produced by the water jet pump, whereby 31.0 g of distillate was produced in about 3 hours. 23.6 g of 2-cyano-1,3-butadiene was obtained from the distillate (Yield 58%). In the above process, 1 g of anhydrous sodium hydrogen carbonate was added whereby 28.2 g of distillate was produced in about 3.5 hours. 20.8 g of 2-cyano-1,3-butadiene was obtained (Yield 51%).

EXAMPLE 29

The process of Example 23 was repeated except for the addition of a solution of 1 g of meta sodium silicate in 5 g of water and heating at 105°–110°C under the pressure of 30–40 mm Hg produced by the water jet pump, whereby 39.1 g of distillate was produced in about 40 minutes. 25.6 g of 2-cyano-1,3-butadiene was obtained from the distillate (Yield 63%). In the above process, 1 g of anhydrous meta-sodium silicate was added, whereby 26.4 g of distillate was produced in about 37 minutes. 17 g of 2-cyano-1,3-butadiene was obtained (Yield 44%).

EXAMPLE 30

The process of Example 23 was repeated except for the addition of a solution of 1 g of meta-potassium borate in 10 g of water and heating at 120°C under the reduced pressure of 40–50 mm Hg produced by the water jet pump, whereby 45.3 g of a distillate was produced in about 60 minutes. 27.3 g of 2-cyano-1,3-butadiene was obtained from the distillate (Yield 67%). In the above process, 1 g of anhydrous meta-potassium borate was added, whereby 28.1 g of distillate was produced in about 53 minutes. 20.4 g of 2-cyano-1,3-butadiene was obtained (Yield 50%).

EXAMPLE 31

The process of Example 23 was repeated except for the addition of a solution of 1.5 g of $Na_3PO_4.12 H_2O$ in 20 g of water and heating at 105°–110°C under the reduced pressure of 30 mm Hg produced by the water jet pump whereby 51.8 g of distillate was produced in about 34 minutes. 22.8 g of 2-cyano-1,3-butadiene was obtained from the distillate (Yield 56%). In said process, 1.5 g of anhydrous $Na_3PO_4.12H_2O$ was added, whereby 27.5 g of distillate was produced in about 26 minutes. 19.6 g of 2-cyano-1,3-butadiene was obtained from the distillate (Yield 48%).

EXAMPLE 32

16 G of pellets of $\alpha$-alumina having diameters of 5 mm was added to a solution of 4.0 g of potassium carbonate in 50 cc of water. The mixture was condensed and dried while stirring, and the resulting catalyst was dried at 120°C overnight. In a 100 cc round flask equipped with a magnetic stirrer and a Liebig condenser, 50 g of 2-cyano-3-hydroxy-1-butene and 4 g of the dried catalyst were charged, and the mixture was heated at 105°–110°C under the reduced pressure of 30 mm Hg produced by a water jet pump, whereby 38.0 g of distillate was produced in about 64 minutes. The distillate was separated into a water phase and an organic phase. From the organic phase, 29.9 g of 2-cyano-1,3-butadiene was obtained (Yield 73.5%). In the above process, 1 g of anhydrous potassium carbonate was substituted for the catalyst, whereby 30.9 g of the distillate was produced in about 48 minutes. 24.0 g of 2-cyano-1,3-butadiene was obtained from the distillate (Yield 59.1%).

EXAMPLE 33

The process of Example 32 was repeated except for the addition of 4 g of catalyst of 20 wt % of $K_2CO_3$ supported on granular $\alpha$-alumina and heating at 120°C under the reduced pressure of 40–50 mm Hg produced by a water jet pump, whereby 41.6 g of distillate was produced in about 60 minutes. 31.6 g of 2-cyano-1,3-butadiene was obtained from the distillate (Yield 77.7%).

EXAMPLE 34

The process of Example 32 was repeated except for the addition of 4 g of a catalyst of 20 wt % of $K_2CO_3$ supported on granular $SiO_2$—$Al_2O_3$, and heating at 138°–140°C under the reduced pressure of 70–80 mm Hg produced by a water jet pump, whereby 39.4 g of distillate was produced in about 21 minutes. 29.3 g of 2-cyano-1,3-butadiene was obtained from the distillate (Yield 72.1%).

EXAMPLE 35

The process of Example 32 was repeated except for the addition of 3 g of catalyst of 20 wt % of $K_2CO_3$ supported on silica powder, and heating at 140°C under the reduced pressure of 70–80 mm Hg produced by a water jet pump, whereby 38.3 g of distillate was produced in about 1.3 hours. 29.8 g of 2-cyano-1,3-butadiene was obtained from the distillate (Yield 73.2%).

EXAMPLE 36

The process of Example 32 was repeated except for the addition of 2 g of catalyst of 20 wt % of $K_2CO_3$ supported on activated carbon and heating at 105°–110°C under the reduced pressure of 30 mm Hg by a water jet pump, whereby 34.4 g of distillate was produced in about 80 minutes. 25.9 g of 2-cyano-1,3-butadiene was obtained from the distillate (Yield 63.6%).

EXAMPLE 37

The process of Example 32 was repeated except for the addition of 8 g of a catalyst of 10 wt % of $K_2CO_3$ supported on α-alumina (diameter of 5 mm) and heating at 138°–140°C under the reduced pressure of 80–90 mm Hg produced by a water jet pump, whereby 38.5 g of the distillate was produced in about 21 minutes. 29.4 g of 2-cyano-1,3-butadiene was obtained from the distillate (Yield 72.3%).

EXAMPLE 38

The process of Example 32 was repeated except for the addition of 2.7 g of a catalyst of 30 wt % of $K_2CO_3$ supported on α-alumina (diameter of 5 mm) and heating at 140°C under the pressure of 70–90 mm Hg produced by a water jet pump, whereby 39.1 g of distillate was produced in about 24 minutes. 29.6 g of 2-cyano-1,3-butadiene was obtained from the distillate (Yield 72.7%).

EXAMPLE 39

The process of Example 32 was repeated except for the addition of 1 g of a catalyst of 20 wt % NaOH supported on granular α-alumina (diameter of 5 mm) and heating at 105°–110°C under the reduced pressure of 20–30 mm Hg produced by a water jet pump, whereby 38.5 g of distillate was obtained in about 3 hours. 30.5 g of 2-cyano-1,3-butadiene was obtained from the distillate (Yield 75.1%). In the above process, 0.28 g of NaOH powder was substituted as the catalyst, whereby 20.4 g of 2-cyano-1,3-butadiene was obtained (Yield 50.1%).

EXAMPLE 40

The process of Example 32 was repeated except for the addition of 5 g of a catalyst of 18 wt % of 1,8-diaza-bicyclo[5,4,0] undecene-7 supported on α-alumina (diameter of 5 mm) and heating at 105°–110°C under the reduced pressure of 30–40 mm Hg produced by a water jet pump, whereby 38.6 g of distillate was produced in about 1.7 hours. 30.1 g of 2-cyano-1,3-butadiene was obtained from the distillate (Yield 74.1%). In the above process, 0.97 g of 1,8-diaza-bicyclo[5,4,-0]undecene-7 was substituted as the catalyst, whereby 32.0 g of the distillate was produced in about 1.3 hours. 23.5 g of 2-cyano-1,3-butadiene was obtained from the distillate (Yield 57.9%).

EXAMPLE 41

The process of Example 32 was repeated except for the addition of 20 g of a catalyst of 20 wt % of potassium acetate supported on silica gel (24–35 mesh) and heating at 140°C under the reduced pressure of 70–80 mm Hg produced by a water jet pump, whereby 28.0 g of the distillate was produced in about 2.8 hours. 23.0 g of 2-cyano-1,3-butadiene was obtained from the distillate (Yield 56.6%). In the above process, 4 g of potassium acetate was substituted as the catalyst, whereby 27.9 g of distillate was produced in about 3.5 hours. 20.3 g of 2-cyano-1,3-butadiene was obtained from the distillate (Yield 49.9%).

EXAMPLE 42

The process of Example 32 was repeated except for the addition of 6 g of a catalyst of 15 wt % of tri-n-butyl phosphine supported on a pumice powder (8–10 mesh) and heating at 80°C under the reduced pressure of 30 mm Hg produced by a water jet pump, whereby 18.3 g of distillate was produced in about 3.5 hours. 9.4 g of 2-cyano-1,3-butadiene was obtained from the distillate (Yield 23.1%). In the above process, 1 g of tri-n-butyl phosphine was substituted as the catalyst, whereby 9.9 g of distillate was produced in about 4 hours. 4.9 g of 2-cyano-1,3-butadiene was obtained from the distillate (Yield 12.0%).

EXAMPLE 43

The process of Example 32 was repeated except for the addition of 8 g of a catalyst [prepared by immersing 2 g of 50% sodium methoxidemethanol into 16 g of synthetic zeolite (14–30 mesh) four times and drying under reduced pressure] and heating at 80°C under the reduced pressure of 30 mm Hg produced by a water jet pump, whereby 25.3 g of distillate was produced in about 15 hours. 17.6 g of 2-cyano-1,3-butadiene was obtained from the distillate (Yield 43.2%). In the above process, 1.6 g of 50% sodium methoxide-methanol was substituted as the catalyst, whereby 22.8 g of the distillate was produced in 65 minutes. 14.3 g of 2-cyano-1,3-butadiene was obtained from the distillate (Yield 35.1%).

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for producing a conjugated diene containing a cyano group having the formula

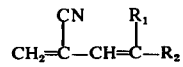

wherein $R_1$ and $R_2$ are hydrogen, $C_1$ to $C_{10}$ alkyl or phenyl which comprises dehydrating the 2-cyano-3-hydroxy-1-olefin compound of the formula

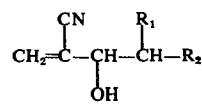

wherein $R_1$ and $R_2$ are as before at 50°–200°C under a reduced pressure of 1 to 600 mm Hg in the presence of an alkaline catalyst wherein the amount of said alkaline catalyst is 0.1–20 weight percent relative to said 2-cyano-3-hydroxy-1-olefin and said conjugated diene is continuously removed by distillation from the reaction system during reaction.

2. A process for producing a conjugated diene containing a cyano group having the formula:

wherein $R_1$ and $R_2$ are hydrogen, $C_1$ to $C_{10}$ alkyl or phenyl which comprises dehydrating in the gas phase the 2-cyano-3-hydroxy-1-olefin of the formula

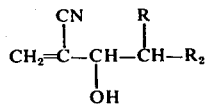

wherein $R_1$ and $R_2$ are as above, at 200°–600°C by passing a said 2-cyano-3-hydroxy-1-olefin over a solid alkaline catalyst wherein said alkaline catalyst is 0.1–20 weight percent relative to said 2-cyano-3-hydroxy-1-olefin.

3. The process according to claim 1, wherein the 2-cyano-3-hydroxyl-1-olefin compound is 2-cyano-3-hydroxy-1-butene, 2-cyano-3-hydroxy-1-pentene, 2-cyano-3-hydroxy-4-methyl-1-pentene, or 2-cyano-3-hydroxy-4-phenyl-butene.

4. The process according to claim 1, wherein the alkaline catalyst is selected from the group consisting of alkali metals, alkaline earth metals and the corresponding hydroxides, oxides, inorganic salts, organic salts or alkoxides thereof, organic amines and organic phosphines.

5. The process according to claim 1, wherein the alkaline catalyst is added in the form of an aqueous solution.

6. The process according to claim 1, wherein the alkaline catalyst is supported on a carrier of alumina gel, silica gel, alumina-silica gel, activated carbon, diatomaceous earth, silicate, pumice, zeolite or other inert carrier.

7. The process according to claim 1, wherein the dehydration is performed by a liquid phase method by heating the mixture of the 2-cyano-3-hydroxy-1-olefin compound and the alkaline material at 50°–200°C under a reduced pressure of 1–600 mm Hg.

* * * * *